(12) United States Patent
Rosen et al.

(10) Patent No.: US 10,527,689 B2
(45) Date of Patent: Jan. 7, 2020

(54) SYSTEM AND METHOD FOR SPIRAL VOLUME IMAGING

(71) Applicant: THE GENERAL HOSPITAL CORPORATION, Boston, MA (US)

(72) Inventors: Matthew S. Rosen, Somerville, MA (US); Mathieu Sarracanie, Somerville, MA (US); Najat Salameh, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 254 days.

(21) Appl. No.: 15/125,860

(22) PCT Filed: Mar. 13, 2015

(86) PCT No.: PCT/US2015/020517
§ 371 (c)(1),
(2) Date: Sep. 13, 2016

(87) PCT Pub. No.: WO2015/138946
PCT Pub. Date: Sep. 17, 2015

(65) Prior Publication Data
US 2017/0010339 A1  Jan. 12, 2017

Related U.S. Application Data

(60) Provisional application No. 61/953,370, filed on Mar. 14, 2014.

(51) Int. Cl.
*G01R 33/34* (2006.01)
*G01R 33/44* (2006.01)
(Continued)

(52) U.S. Cl.
CPC ...... *G01R 33/34046* (2013.01); *A61B 5/0402* (2013.01); *A61B 5/055* (2013.01);
(Continued)

(58) Field of Classification Search
None
See application file for complete search history.

(56) References Cited

U.S. PATENT DOCUMENTS 4,774,468 A   9/1988 Bydder
5,050,605 A   9/1991 Eydelman et al.
(Continued)

FOREIGN PATENT DOCUMENTS

JP   S60253857 A   12/1985
JP   H0329639 A    2/1991
(Continued)

OTHER PUBLICATIONS

Haishi Tomoyuki, Nuclear Magnetic Resonance Image Diagnostic System, Feb. 12, 2010, JP2010029313 (translation).*
(Continued)

*Primary Examiner* — James M Kish
(74) *Attorney, Agent, or Firm* — Quarles & Brady LLP (57) ABSTRACT

A system and method for system for performing a magnetic resonance imaging (MRI) process using an MRI system is provided. A coil system includes a substrate configured to follow a contour of a portion of a subject to be imaged by the MRI system and at least one coil coupled to the substrate and forming a spiral pattern.

29 Claims, 11 Drawing Sheets (51) Int. Cl.
  *G01R 33/561* (2006.01)
  *G01R 33/563* (2006.01)
  *A61B 5/0402* (2006.01)
  *A61B 5/055* (2006.01)
  *A61B 5/08* (2006.01)
  *G01R 33/56* (2006.01)
  *G01N 24/08* (2006.01)

(52) U.S. Cl.
  CPC .......... *A61B 5/08* (2013.01); *G01R 33/34084* (2013.01); *G01R 33/445* (2013.01); *G01R 33/5601* (2013.01); *G01R 33/5614* (2013.01); *G01R 33/5635* (2013.01); *G01N 24/084* (2013.01)

(56) References Cited

U.S. PATENT DOCUMENTS

| | | | |
|---|---|---|---|
| 6,023,166 | A | 2/2000 | Eydelman |
| 8,588,938 | B2 | 11/2013 | Lloyd et al. |
| 2001/0037063 | A1* | 11/2001 | Albert .................. G01R 33/445 600/420 |
| 2003/0062896 | A1 | 4/2003 | Wong et al. |
| 2004/0112523 | A1 | 6/2004 | Crom et al. |
| 2004/0113613 | A1 | 6/2004 | Markl et al. |
| 2005/0088179 | A1 | 4/2005 | Sato |
| 2005/0253582 | A1 | 11/2005 | Giaquinto et al. |
| 2006/0091881 | A1 | 5/2006 | Clarke et al. |
| 2007/0085544 | A1 | 4/2007 | Viswanathan |
| 2008/0007250 | A1 | 1/2008 | Wiggins |
| 2008/0103383 | A1 | 5/2008 | Van Der Kouwe et al. |
| 2009/0179643 | A1 | 7/2009 | Lin |
| 2010/0033173 | A1 | 2/2010 | Gleich et al. |
| 2010/0060282 | A1 | 3/2010 | Shvartsman et al. |
| 2012/0146643 | A1 | 6/2012 | Saha et al. |

FOREIGN PATENT DOCUMENTS

| | | |
|---|---|---|
| JP | H08500436 A | 1/1996 |
| JP | 2000262488 A | 9/2000 |
| JP | 2005503907 A | 2/2005 |
| JP | 2005124692 A | 5/2005 |
| JP | 2009511232 A | 3/2009 |
| JP | 2010029313 A | 2/2010 |
| JP | 2010124911 A | 6/2010 |
| KR | 20120097855 A | 9/2012 |
| KR | 20140030997 A | 3/2014 |
| WO | 9324848 A1 | 12/1993 |

OTHER PUBLICATIONS

Coffey, Aaron et al., "A Large Volume Double Channel 1H-X RF Probe for Hyperpolarized Magnetic Resonance at 0.0475 Tesla." J. Magn Reson. Jul. 2012, pp. 3.*
Mark Lorch, "Ten weird and terrifying medical instruments from the past", Medical Press, Jan. 22, 2014. pp. 1-6.*
Richard Moss, "How Star Wars helped a gneration of children undergo brain scans." Museum Crush, published Feb. 8, 2018, pp. 1-9.*
International Search Report and Written Opinion dated Jun. 29, 2015 for International Application No. PCT/US2015/020517.
Vesanen, P. et al: "Hybrid Ultra-Low Field MRI and Magnetoencephalography System Based on a Commercial Whole-Head Neuromagnetometer", Jun. 2013; Mag. Res. in Medicine 69:1795-1804 (2013); (retrieved on May 31, 2015); Retrieved from the internet: URL http://onlinelibrary.wiley.com/doi/10.1002/mm.24413/abstract: p. 1796, col. 2, l ines 17-56.
Lapierre, et al., Parallel Imaging and Acceleration in the Johnson Noise Dominated Regime, Proc. Intl. Soc. Mag. Reson. Med., 2013, 21:2772.
European Patent Office, Extended European Search Report, Application No. 15762356.2, dated Nov. 28, 2017, 8 pages.

* cited by examiner

FIG. 7

SYSTEM AND METHOD FOR SPIRAL VOLUME IMAGING

CROSS-REFERENCE TO RELATED APPLICATIONS

The application represents the U.S. National Stage of International Application No. PCT/US2015/020517, filed Mar. 13, 2015 which is based on, claims priority to, U.S. Provisional Application Ser. No. 61/953,370, filed Mar. 14, 2014, both of which are incorporated herein by reference for all purposes.

STATEMENT REGARDING FEDERALLY SPONSORED RESEARCH

This invention was made with government support under W81XWH-11-2-076 awarded by the Department of Defense. The government has certain rights in the invention.

BACKGROUND

The present disclosure relates to systems and methods for a magnetic resonance imaging (MRI) and, more particularly, to a spiral coil architecture and method of using such coil during an imaging process When a substance such as human tissue is subjected to a uniform magnetic field (polarizing field $B_0$), the individual magnetic moments of the excited nuclei in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

MRI is performed by exciting and detecting emitted MR signals using transmit and receive coils, respectively (often referred to as radio frequency (RF) coils). Transmit/receive coils may include separate coils for transmitting and receiving, multiple coils for transmitting and/or receiving, or the same coils for transmitting and receiving. Transmit/receive coils are also often referred to as Tx/Rx or Tx/Rx coils to generically refer to the various configurations for the transmit and receive magnetic component of an MRI system. These terms are used interchangeably herein.

Presently, MRI systems deployed in clinical environments are high-field systems because high-field systems have historically been the only MRI solution capable of producing clinically useful images. However, high-field MRI systems are large, costly and require specialized facilities. As a result, the size and expense of high-field MRI systems limit their use and render them unavailable in numerous clinical situations that could benefit from MRI.

SUMMARY

Low-field MRI provides a relatively low cost, high availability alternative to high-field MRI. However, low-field MRI presents a number of challenges including relatively weak MR signals and low signal-to-noise ratio. As a result, design of transmit/receive coils plays a significant role in performing satisfactory low-field MRI. To address this, the inventors have developed transmit/receive coil designs to facilitate improved excitation and detection of MR signals suitable for the low-field context.

According to some embodiments, a three-dimensional (3D) transmit/receive coil having a spiral geometry is provided. The transmit/receive coil may be mounted on a form-fitting substrate that, for example, may be contoured to particular anatomy, such as a helmet. The configuration provides a homogeneous magnetic field and high sensitivity over 3D volumes.

In accordance with one aspect of the disclosure, a magnetic resonance imaging (MRI) system is provided that includes a magnet system configured to generate a static magnetic field about at least a region of interest (ROI) of a subject arranged in the MRI system and a plurality of gradient coils configured to establish at least one magnetic gradient field with respect to the static magnetic field. The system also includes a radio frequency (RF) system including a transmit/receive coil. The transmit/receive coil includes a substrate configured to follow a contour of a portion of a subject to be imaged by the MRI system and at least one coil coupled to the substrate and forming a hemispherical spiral pattern.

In accordance with another aspect of the disclosure, a coil system is provided for performing a magnetic resonance imaging (MRI) process using an MRI system. The coil system includes a substrate configured to follow a contour of a portion of a subject to be imaged by the MRI system and at least one coil coupled to the substrate and forming a three-dimensional spiral pattern.

The foregoing and other advantages of the invention will appear from the following description.

DETAILED DESCRIPTION

As discussed above, clinical MRI scanners are predominantly high-field systems, with the vast majority of installed MRI scanners operating at 1.5 or 3 tesla (T). The trend in MRI is to increase the field strength even further to improve image quality and/or reduce scan times. However, while high-field MRI can provide high resolution images at relatively short scan times, the cost of manufacturing, deploying and maintaining a high-field MRI installment is often prohibitive, resulting in significantly limited availability of high-field MRI systems and preventing their use in many clinical applications.

Low-field MRI (e.g., systems that operate at 0.2 T and below) provides a relatively low cost, high availability alternative to high-field MRI. However, low-field MRI presents a number of challenges resulting from the low-field strengths employed, including significantly reduced signal-to-noise ratio (SNR). In particular, SNR of an MR signal is related to the strength of the main magnetic field B0, which is a significant factor driving high-field MRI and the trend towards higher field strengths. Low-field MRI produces relatively weak MR signals resulting in substantially lower SNR. Thus, transmit/receive coil design is an important factor in transmitting excitation pulse sequences and detecting emitted MR signals as effectively as possible.

The inventors have appreciated that the low field strengths employed in low-field MRI facilitate the design of transmit/receive coils that are not applicable and/or possible in the high-field context. For example, to transmit excitation pulse sequences and to detect emitted MR signal, transmit/receive coils must resonate at a frequency dependent on the strength of the B0 field. Accordingly, transmit/receive coils in the high-field regime must resonate at significantly higher frequencies than their low-field counterparts. Because of the inverse relationship between the length of a conducting path and the wavelength of the resonant frequency/frequencies in a resonant circuit (i.e., the frequencies at which a coil can produce and detect magnetic fields), the conducting paths of high-field transmit/receive coils are required to be very short.

The inventors have recognized that the low frequencies involved in low-field MRI permit the conducting paths of transmit/receive coils to be quite long, allowing for coil designs that are not suitable (or useable) for high-field MRI due to the severe constraints on conductive path length imposed by the high frequencies involved in high-field MRI. According to some embodiments, a transmit/receive coil is formed by a single conducting path provided over a three-dimensional surface corresponding to a region of interest. For example, a low-field transmit/receive head coil may be produced by winding a conductor about a substrate manufactured to be worn by a person as a helmet (e.g., a helmet fabricated using 3D printing). According to some embodiments, the conductor is wound in a spiral geometry about the surface of the helmet to provide coverage sufficient (e.g., a hemispherical spiral) to provide pulse sequences to a region of interest (e.g., the brain or a portion thereof) and/or to detect MR signals emitted from the region of interest.

Additionally, clinical high-field MRI systems typically generate a B0 field via a solenoid coil wound about a cylindrical bore into which the patient being imaged is inserted. As such, the B0 field is oriented along the longitudinal axis of the bore and the body inserted into the bore. To perform MRI, transmit/receive coils must produce a B1 field perpendicular to the B0 field and detect emitted MR signals in this transverse direction. This places further restrictions on the geometry for transmit/receive coils designed for high-field MRI.

Low-field MRI facilitates the design of "open" systems in which the B0 field is generated using, for example, bi-planar coils between which a patient being imaged is placed such that the B0 field is oriented perpendicular to the longitudinal axis of the body. Accordingly, transmit/receive coils are arranged to produce and/or detect magnetic fields transverse to this B0 field, allowing for geometries not possible in traditional high-field MRI systems. As a result, bi-planar B0 magnets (or other arrangements that produce a B0 field that is transverse to the axis of the body) allow for the design of transmit/receive coils that produce/detect magnetic fields in the axial direction of the body, some examples of which are described in further detail below. Transmit/receive coils configured as such are not useable with B0 coils that produce magnetic fields aligned with the axis of the body, such as those commonly used in high-field MRI.

The inventors have further appreciated that the low-field context also facilitates the use of different materials to produce transmit/receive coils. For example, conductive paths in transmit/receive coils for high-field MRI are typically fabricated from sheets of copper. In the low-field context, conductive paths can be formed using wire, for example, single strand wire, multi-strand wires (e.g., Litz wires), etc. The term "wire" is used herein to describe conductors having a cross-section characteristic of extrusion such that the cross-section has an axis of symmetry (e.g., such as a generally circular cross-section, rectangular cross-section, etc.), as opposed to conductors formed by milling or cutting copper sheets. A wire may be single stranded wire of suitable gauge, or multi-stranded wire such as a Litz wire. As a result, transmit/receive coils for low-field MRI can be simply and inexpensively produced. It should be appreciated that conductors for the transmit/receive coils described herein can be produced in any suitable way, including not only wire-based designs, but including using conventional high-field techniques of forming coils from conductive sheets, as the aspects are not limited in this respect.

The inventors have further appreciated that the factors described above (e.g., the significantly relaxed constraint on conductive path length, the different orientation of the B0 field and/or greater flexibility with respect to the available materials, etc.) allow for a wide variety of coil designs and facilitate producing coils conforming to the particular anatomy being imaged. As a result, a transmit/receive coil can be formed by providing the conductive paths in a three-dimensional configuration about the anatomy being imaged, thus providing a substantially form-fitting transmit/receive coil.

Following below are more detailed descriptions of various concepts related to, and embodiments of, methods and apparatus for providing transmit/receive coils for use in MRI. It should be appreciated that the embodiments described herein may be implemented in any of numerous ways. Examples of specific implementations are provided below for illustrative purposes only. It should be appreciated that the embodiments and the features/capabilities provided may be used individually, all together, or in any combination, as aspects of the technology described herein are not limited in this respect.

Figure 1:
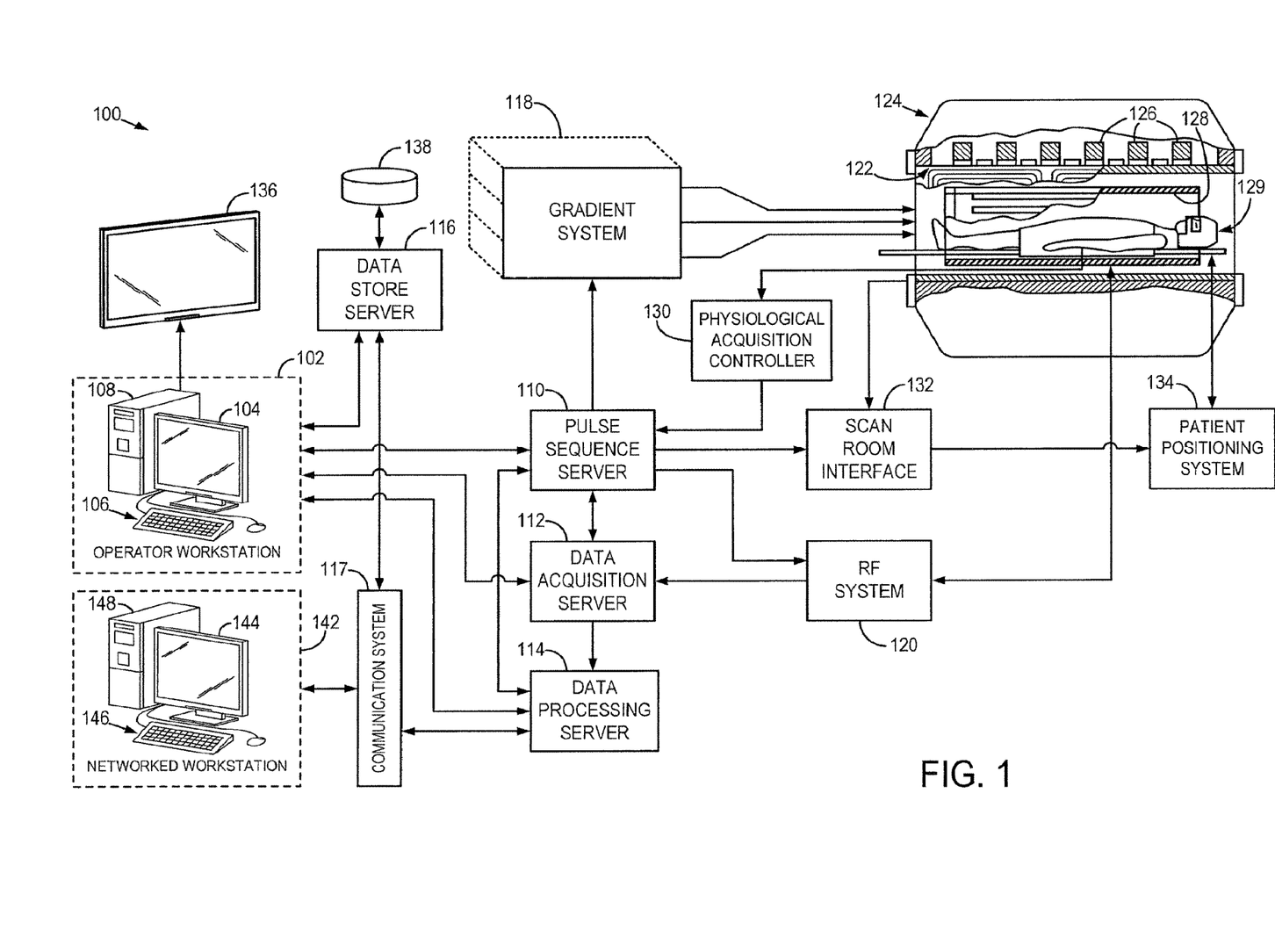
FIG. 1 is a block diagram of an MRI system.

Referring particularly now to FIG. 1, an example of a magnetic resonance imaging (MRI) system 100 is illustrated. The MRI system 100 includes an operator workstation 102, which will typically include a display 104, one or more input devices 106, such as a keyboard and mouse, and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to four servers: a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 117, which may include any suitable network connection, whether wired, wireless, or a combination of both. As an example, the communication system 117 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding magnetic resonance signals. The gradient coil assembly 122 forms part of a magnet assembly 124 that includes a polarizing magnet 126 and a whole-body RF coil 128 and/or transmit/receive coil, such as a head coil 129.

RF waveforms are applied by the RF system 120 to the RF coil 128, or a separate transmit/receive coil, such as the head coil 129, in order to perform the prescribed magnetic resonance pulse sequence. Responsive magnetic resonance signals detected by the RF coil 128, or a separate transmit/receive coil, such as the head coil 129, are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more transmit/receive coils or coil arrays, such as the head coil 129.

The RF system 120 also includes one or more RF receiver channels. Each RF receiver channel includes an RF preamplifier that amplifies the magnetic resonance signal received by the coil 128/129 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \quad (1);$$

and the phase of the received magnetic resonance signal may also be determined according to the following relationship:

$$\varphi = \tan^{-1}\left(\frac{Q}{I}\right). \quad (2)$$

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography (MRA) scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 102, or in a different facility, such as a different healthcare institution or clinic.

The networked workstation 142, whether within the same facility or in a different facility as the operator workstation 102, may gain remote access to the data processing server 114 or data store server 116 via the communication system 117. Accordingly, multiple networked workstations 142 may have access to the data processing server 114 and the data store server 116. In this manner, magnetic resonance data, reconstructed images, or other data may exchanged between the data processing server 114 or the data store server 116 and the networked workstations 142, such that the data or images may be remotely processed by a networked workstation 142. This data may be exchanged in any suitable format, such as in accordance with the transmission control protocol (TCP), the internet protocol (IP), or other known or suitable protocols.

Figure 2:
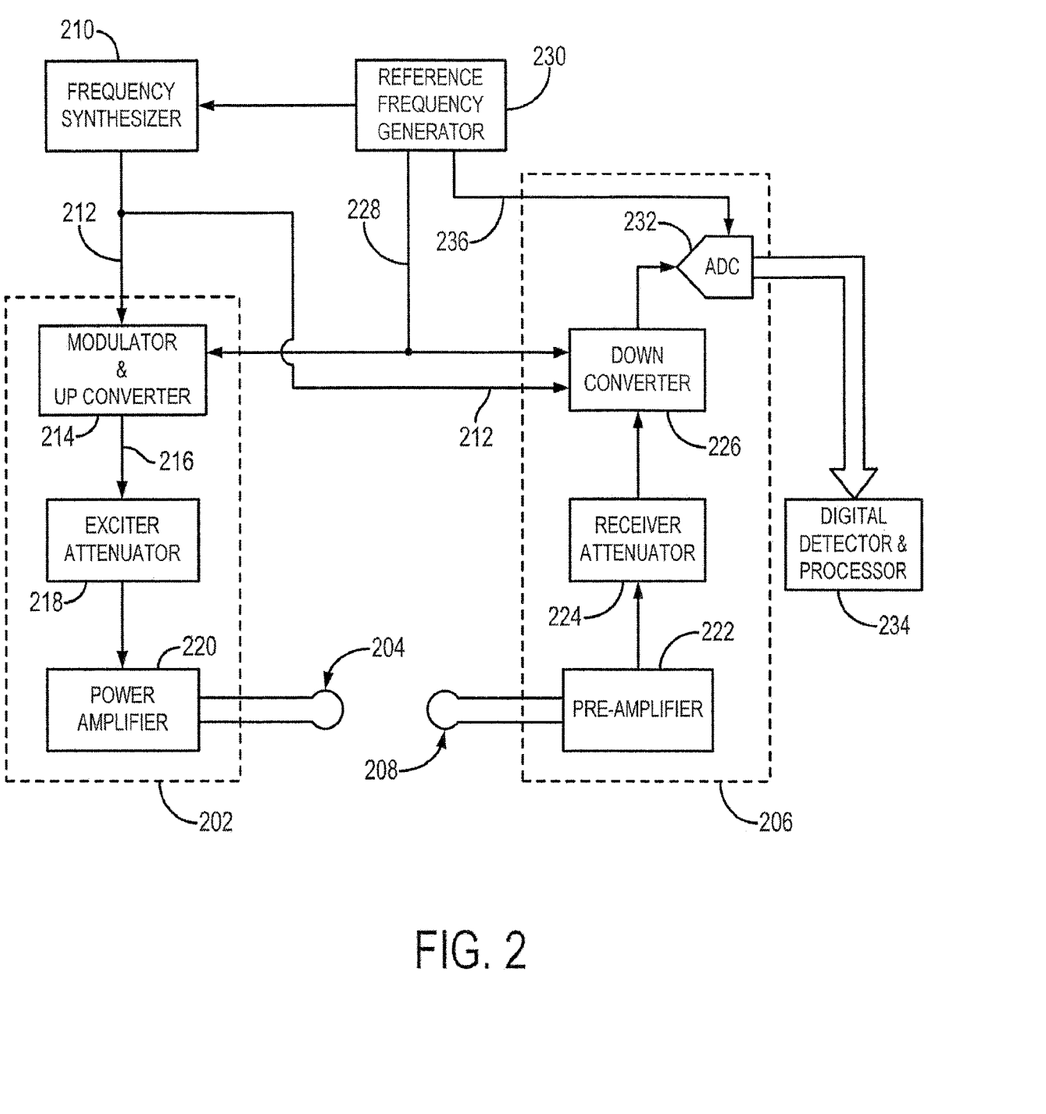
FIG. 2 is a block diagram of an RF system of an MRI system.

With reference to FIG. 2, the RF system 120 of FIG. 1 will be further described. The RF system 120 includes a transmission channel 202 that produces a prescribed RF excitation field. The base, or carrier, frequency of this RF excitation field is produced under control of a frequency synthesizer 210 that receives a set of digital signals from the pulse sequence server 110. These digital signals indicate the frequency and phase of the RF carrier signal produced at an output 212. The RF carrier is applied to a modulator and up converter 214 where its amplitude is modulated in response to a signal, R(t), also received from the pulse sequence server 110. The signal, R(t), defines the envelope of the RF excitation pulse to be produced and is produced by sequentially reading out a series of stored digital values. These stored digital values may be changed to enable any desired RF pulse envelope to be produced.

The magnitude of the RF excitation pulse produced at output 216 is attenuated by an exciter attenuator circuit 218 that receives a digital command from the pulse sequence server 110. The attenuated RF excitation pulses are then applied to a power amplifier 220 that drives the RF transmission coil 204.

The RF system 120 includes a receiver channel 206. The MR signal produced by the subject is picked up by the RF receiver coil 208 and applied through a preamplifier 222 to the input of a receiver attenuator 224. The receiver attenuator 224 further amplifies the signal by an amount determined by a digital attenuation signal received from the pulse sequence server 110. The received signal is at or around the Larmor frequency, and this high frequency signal is down converted in a two step process by a down converter 226. The down converter 226 first mixes the MR signal with the carrier signal on line 212 and then mixes the resulting difference signal with a reference signal on line 228 that is produced by a reference frequency generator 230. The down converted MR signal is applied to the input of an analog-to-digital ("A/D") converter 232 that samples and digitizes the analog signal. The sampled and digitized signal is then applied to a digital detector and signal processor 234 that produces 16-bit in-phase (I) values and 16-bit quadrature (Q) values corresponding to the received signal. The resulting stream of digitized I and Q values of the received signal are output to the data acquisition server 112. In addition to generating the reference signal on line 228, the reference frequency generator 230 also generates a sampling signal on line 236 that is applied to the ND converter 232.

Figure 3A:
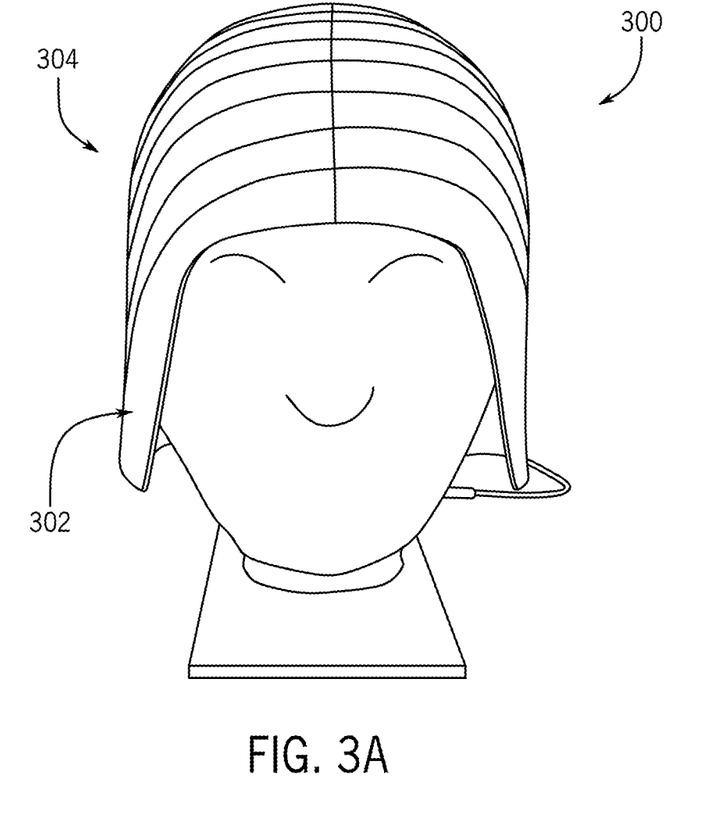
FIG. 3A is a front elevational view of a transmit/receive coil in accordance with the present disclosure and configured for use with systems such as described with respect to FIGS. 1, 2, and 4.
Figure 3B:
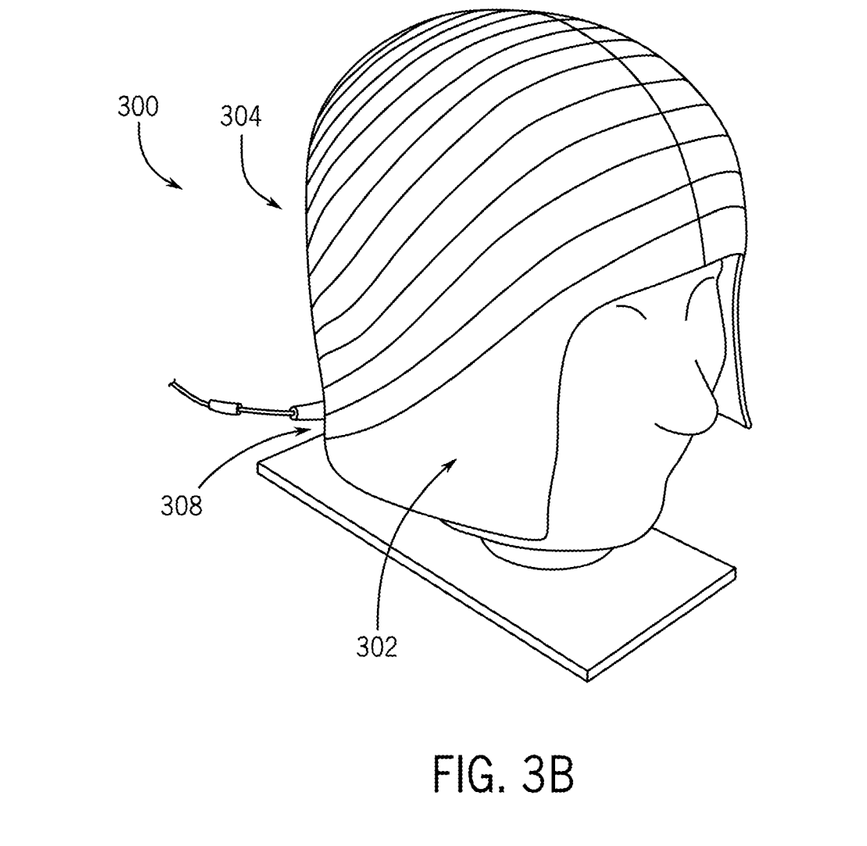
FIG. 3B is a side perspective view of the transmit/receive coil of FIG. 3A.
Figure 3C:
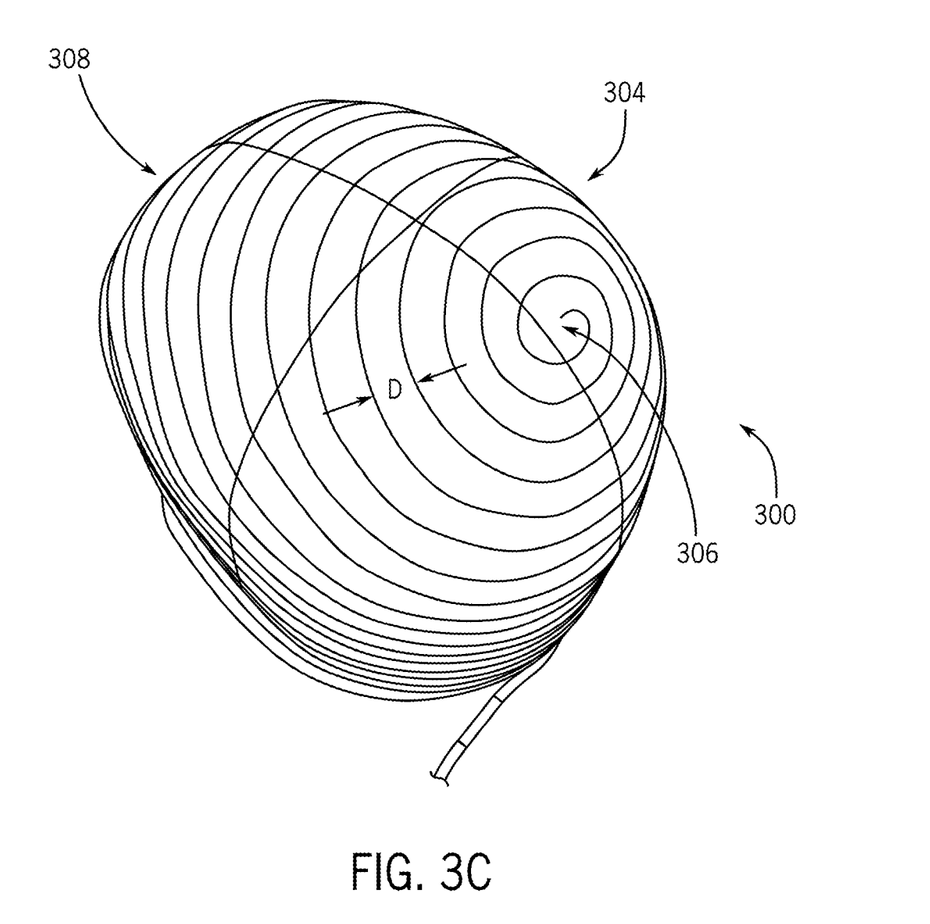
FIG. 3C is a rear perspective view of the transmit/receive coil of FIGS. 3A and 3B.

Referring to FIGS. 3A through 3C, a transmit/receive coil design, illustrated as a form fitting spiral (FFS) transmit/receive coil 300, is illustrated. As will be described, the FFS transmit/receive coil 300 provides a homogeneous magnetic field and high sensitivity over three-dimensional volumes. The FFS transmit/receive coil 300 includes a substrate or housing 302 to which or on which a spiral coil 304 is coupled. The substrate 302 may be highly form fitting. For example, the substrate 302 may be created using a three-dimensional (3D) printer to specifically contour to anatomy, such as a head in the illustrated example. Thus, the substrate 302 may be formed of a material suitable for 3D printing. Likewise, the windings of the coil 304 may be tailored to comfortably fit the underlying anatomy (in this example, the head) and achieve a desired filling factor, which may be a maximized filling factor.

The coil 304, as illustrated, forms a spiral. The coil 304 may spiral out from a center 306 aligned with a crown of the head of the subject to a perimeter 308 encircling the head of the subject. Thus, the coil 304 may be configured to spiral out from the center 306 to the perimeter 308. The coil 304 may be arranged to have a uniform or substantially uniform distance (D) between adjacent portions of the spiral. In other configurations, the distance D may be non-uniform and may vary as the spiral moves from the center 306 to the perimeter 308. In any case, the coil 304 forms a hemispherical spiral pattern that provides high magnetic field homogeneity. The spiral pattern advantageously controls or removes the need for coil decoupling strategies common in many transmit/receive coils. As opposed to conventional surface coils that provide high sensitivity but suffer from high magnetic field inhomogeneity and need a separate coil for transmit operations, the above-described spiral coil of the present disclosure can be tuned to provide high homogeneity, while maintaining high sensitivity over large field of views in a streamlined design. The FFS transmit/receive coil 300 can be used for both transmit and receive operations.

The above-described FFS transmit/receive coil 300, and other FFS coils tailored to other anatomy or ROIs, can be used for NMR or MRI of human body parts, like the head, arm, leg, hand, or any extremities to provide high sensitivity with any type of MRI sequence including gradient-echo based, spin echo based sequences, and fully-refocused sequences, such as balanced-steady state free precession (b-SSFP). Notably, regardless of the underlying geometry of the substrate or ROI, the FFS transmit/receive coils of the present disclosure can be particularly advantageously used for MRI sequences utilizing high flip angle homogeneity, such as the b-SSFP pulse sequence.

Figure 4:
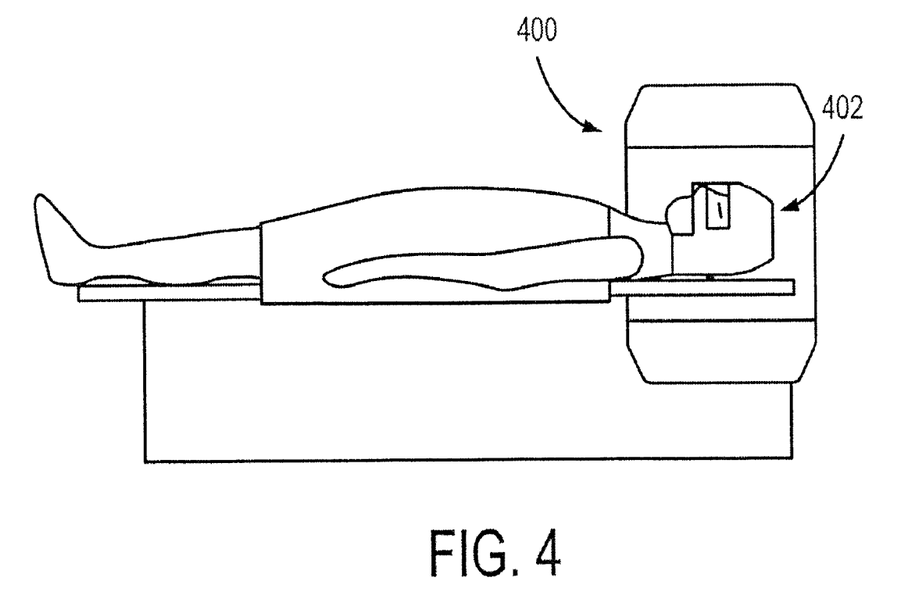
FIG. 4 is a schematic diagram of a low-field MRI system that may be used with the transmit/receive coil of FIGS. 3A, 3B, and 3C.

These FFS transmit/receive coils can also be used with low field magnetic resonance imaging (lfMRI) systems. For example, lfMRI may be advantageous for imaging subjects otherwise excluded from conventional MRI due to metal implants, pacemakers, and the like. The FFS transmit/receive coils can be used in MRI-based security check units in areas with dense population traffic. For example, referring to FIG. 4, the basic MR systems and principles described above may be used to inform the design of other MR systems that share similar components, but operate at very-different parameters. In one example, a low-field magnetic resonance imaging (lfMRI) system utilizes much of the above-described hardware, but has substantially reduced hardware requirements and a smaller hardware footprint. For example, referring to FIG. 4, a system is illustrated that, instead of a 1.5 T or greater static magnetic field, utilizes a substantially smaller magnetic field. That is, FIG. 4, as a non-limiting example, the magnetic field used in the system 400 may be less than 10 mT. As one particular example, the system 400 may be a 6.5 mT electromagnet-based scanner that is capable of imaging objects up to, for example, 15.6 cm in diameter. The system 400 may use a transmit/receive coil 402 such as described above with respect to FIG. 3.

Figure 5A:
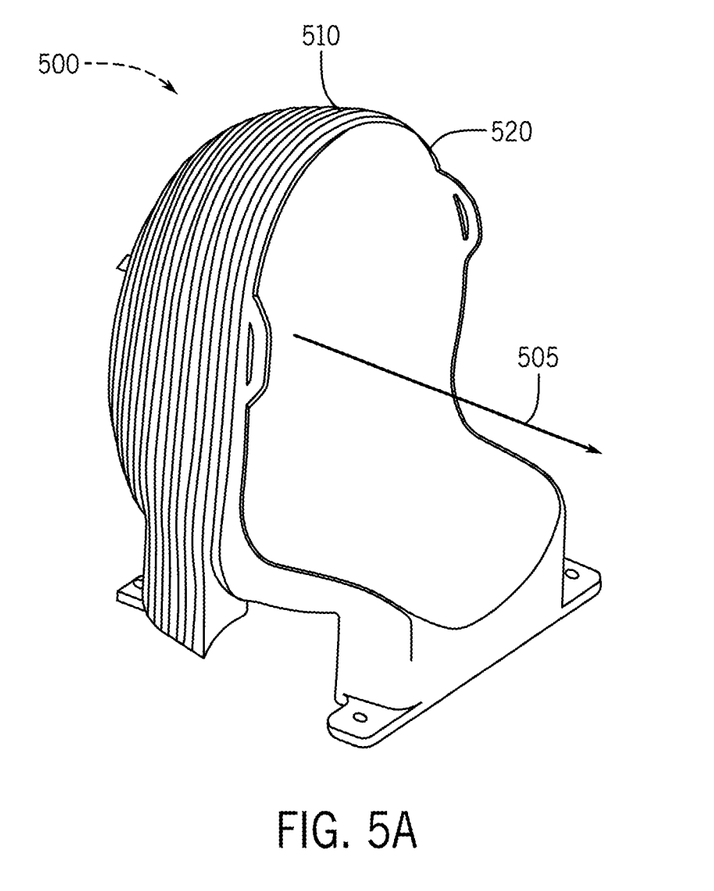
FIG. 5A is a perspective view of a transmit/receive coil, in accordance with some embodiments.
Figure 5B:
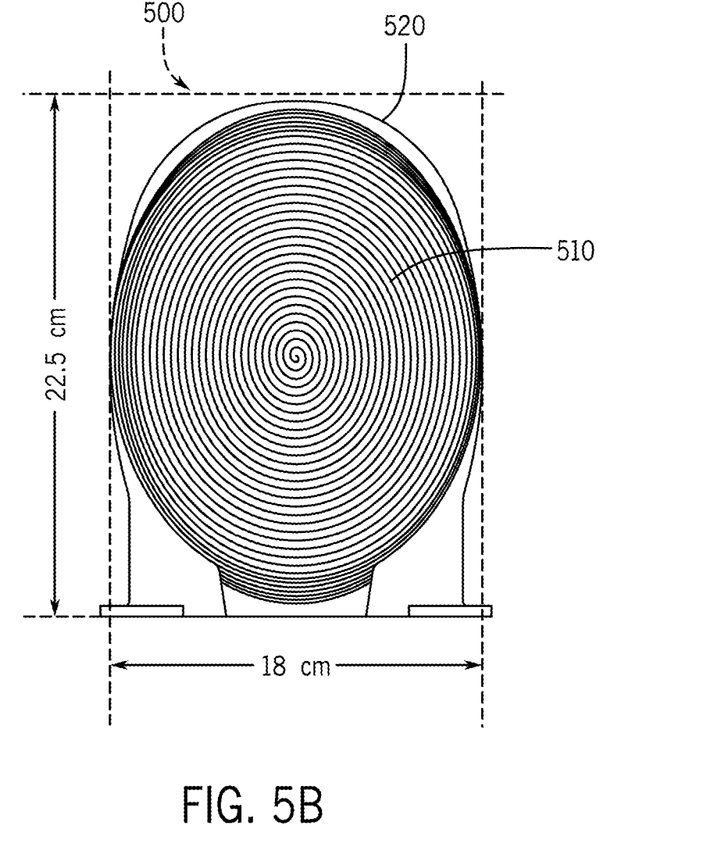
FIG. 5B is a top view of the transmit/receive coil illustrated in FIG. 5A.
Figure 5C:
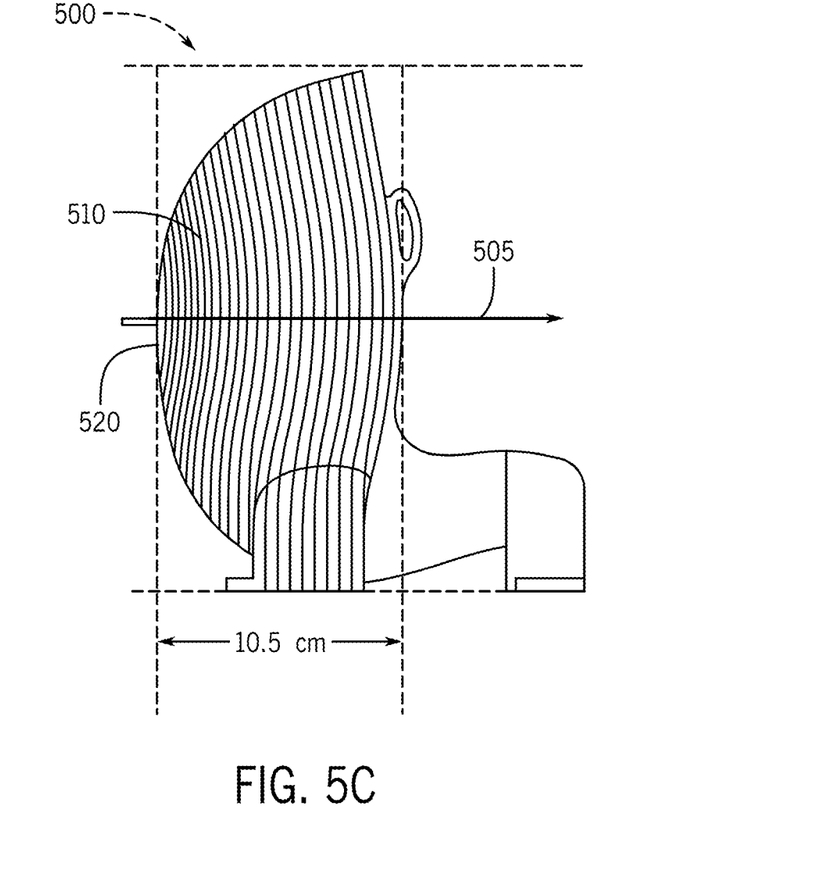
FIG. 5C is a side view of the transmit/receive coil illustrated in FIGS. 5A and 5B.

FIGS. 5A-5C illustrate several views of another design for a transmit/receive head coil for use in low-field MRI, in accordance with some embodiments. Transmit/receive coil 500 includes a substrate 520 formed to accommodate the head of a subject to be imaged. The substrate may be formed with grooves in which conductor 510 is provided (e.g., wound) according to a desired geometry. The substrate may be, for example, created via computer assisted design (CAD) and then produced using 3D printing techniques, or the substrate may be formed using any other suitable technique. The substrate includes a helmet portion to accommodate the head and a support base so that a patient can comfortably rest the head within the helmet in a supine position.

As illustrated, conductor 510 is wound about substrate 520 in a spiral geometry so that, when operated, the coil produces a magnetic field in the direction indicated by arrow 505, and can detect magnetic fields oriented in the same direction. According to some embodiments, conductor 510 comprises a single continuous wire forming a single channel transmit and receive coil. In some embodiments, conductor 510 is a single stranded wire of appropriate gauge. In some embodiments, conductor 510 is a multi-stranded wire such as a Litz wire. A Litz wire is a bundle of individually insulated wire conductors that are bundled, twisted or woven together. The inventors have appreciated that using a Litz wire can produce a coil having the same inductance as a single stranded wire of the same gauge, but having a fraction of the resistance at the operating frequencies characteristic of low-field MRI. As a result, resistive losses are substantially reduced, thereby decreasing the noise of the transmit/receive coil and increasing SNR.

As discussed above, high-field MRI operates at high frequencies (e.g., greater than 64 Mhz) so that conducting paths of RF coils are required to be very short to operate correctly. The exemplary transmit/receive coil 300 illustrated in FIG. 3 has a conducting path of approximately 7 meters and the exemplary transmit/receive coil 500 in FIGS. 5A-5C has a conducting path of approximately 14 meters. Thus, the length of the conductors in these exemplary transmit/receive coils are well beyond (by an order of magnitude or more) the limit imposed by the high frequencies of the high-field MRI regime, and therefore the configurations illustrated in FIG. 3 and FIGS. 5A-5C are made possible by the low field strengths of the low-field regime.

Additionally, at least in part due to the limits placed on conductive path length in high-field MRI, transmit/receive coils are frequently single turn conductive loops in the high-field context. The substantial relaxation of this constraint in the low-field context allows for coils having a plurality of turns. As illustrated in FIG. 3 and FIGS. 5A-5C, the coil is arranged to have a plurality of turns. According to some embodiments, the conductor forming a transmit receive coil is arranged in a three-dimensional geometry about a region of interest so that it forms a plurality of turns (e.g., 5, 10, 20, 30 turns, etc.). There is no limitation on the number of turns that can be used, provided any design constraints regarding total coil inductance and/or resistance are respected.

Figure 6:
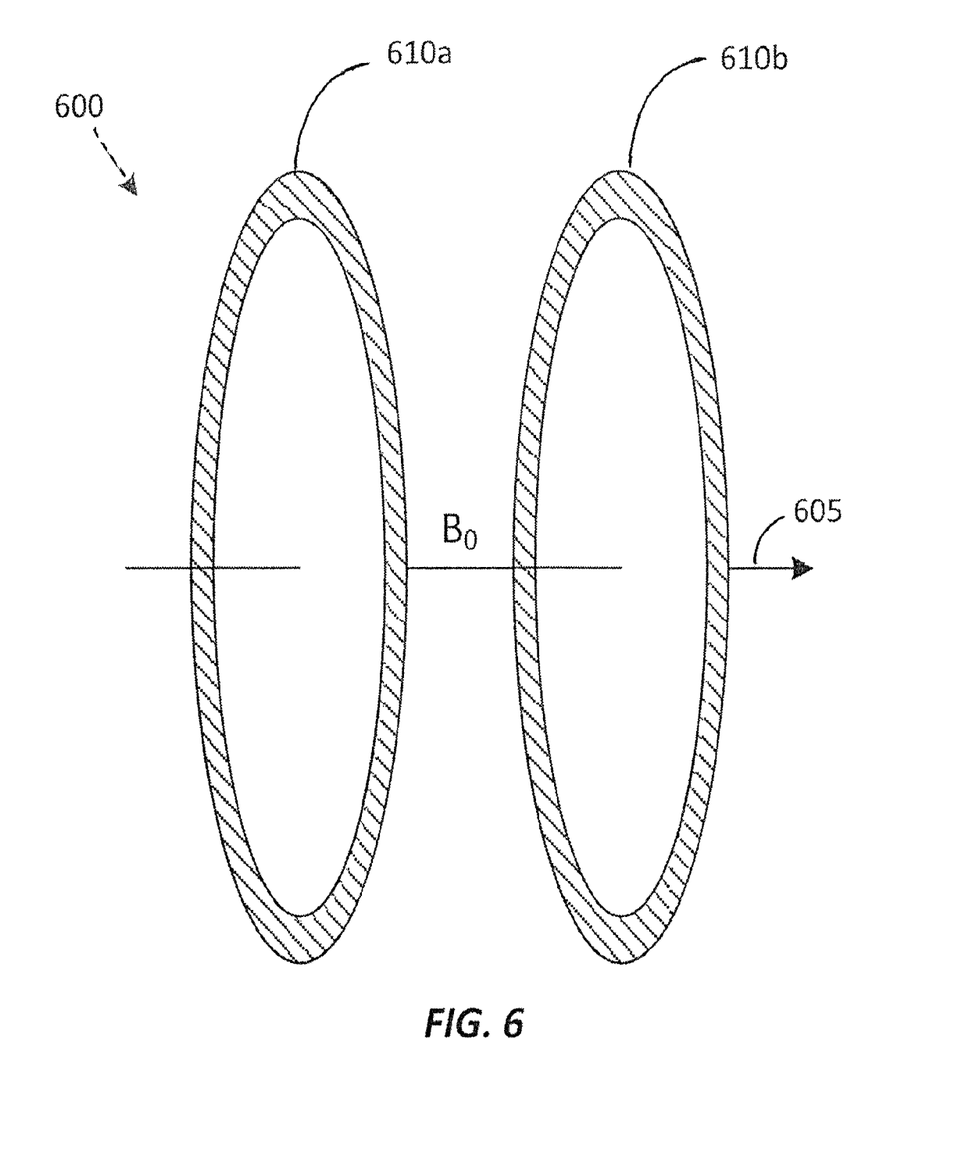
FIG. 6 schematically depicts a bi-planar arrangement for a B0 magnet.

As also discussed above, low-field MRI systems can be constructed using a bi-planar configuration for the B0 magnet. For example, FIG. 6 schematically depicts a magnet 600 to illustrate a bi-planar coil configuration that can be used to generate a B0 field for low-field MRI. As illustrated, the B0 magnet includes coils 610a and 610b that, when operated, produce a B0 field oriented in the direction indicated by arrow 605. When a subject is placed between coils 610a and 610b, B0 is perpendicular to the longitudinal axis of the body of the subject.

Figure 7:
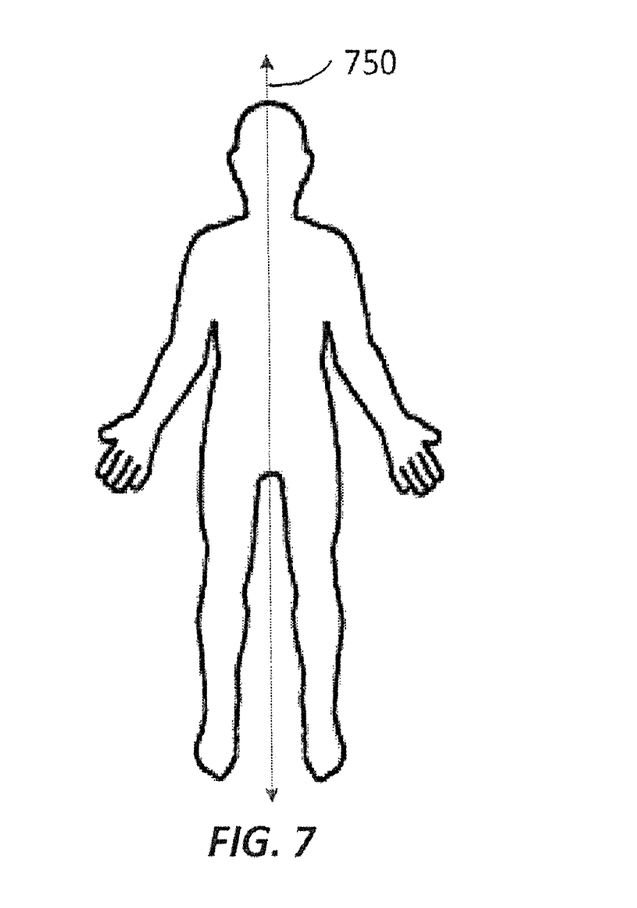
FIG. 7 illustrates an outline of a human body showing the longitudinal axis of the body.

FIG. 7 illustrates the longitudinal axis 750 of the human body, which is perpendicular to the B0 field of magnet 600 both when the subject is placed between the B0 coils in a upright or supine position.

Accordingly, low-field MRI systems having a B0 field oriented as shown in FIG. 6 (perpendicular to the longitudinal axis of the body) permit the use of the transmit/receive coil geometries described herein. By contrast, high-field MRI systems are predominantly produced using a solenoid B0 magnet such that the B0 field is oriented along the longitudinal axis of the body of a subject and the bore into which the subject is inserted, thus requiring a B1 excitation field in a perpendicular direction. As shown in FIGS. 5A-5C, the magnetic field generated by the exemplary transmit/receive coils are also aligned with the longitudinal axis of the wearer of the head coil and therefore these coils are ineffective for transmit and receive for a solenoid-based B0 magnet.

The present invention has been described in terms of one or more embodiments, and it should be appreciated that many equivalents, alternatives, variations, and modifications, aside from those expressly stated, are possible and within the scope of the invention.

The invention claimed is:

1. A magnetic resonance imaging (MRI) system, comprising:
    a magnet system configured to generate a static magnetic field about at least a region of interest (ROI) of a subject arranged in the MRI system;
    a plurality of gradient coils configured to establish at least one magnetic gradient field with respect to the static magnetic field;
    a radio frequency (RF) system including a transmit and receive coil comprising:
        a substrate configured to follow a contour of a portion of the subject to be imaged by the MRI system;
        at least one coil coupled to the substrate and forming a hemispherical spiral pattern; wherein the hemispherical spiral pattern includes a distance between adjacent portions of the at least one coil that is uniform;
            wherein the at least one coil is configured to originate and spiral out from a center point configured to be aligned with an apex of a crown of a head of the subject; and
            wherein the at least one coil is further configured by spiraling out to encircle a perimeter of the head of the subject.

2. The MRI system of claim 1 wherein the static magnetic field is a low-field static magnetic field.

3. The MRI system of claim 1 wherein the static magnetic field is less than 10 mT.

4. The MRI system of claim 1 wherein the transmit and receive coil is sized to image a periphery of the subject.

5. The MRI system of claim 1 wherein the MRI system is configured to perform a pulse sequence to perform an imaging process and wherein the at least one coil is configured to perform transmit and receive operations during performance of the pulse sequence.

6. The MRI system of claim 5 wherein the pulse sequence includes a balance steady state free precession (b-SSFP) pulse sequence.

7. The MRI system of claim 1 wherein the substrate forms a helmet and the portion of the subject is the head, such that the helmet is configured to contour the head of the subject.

8. The MRI system of claim 1 wherein the substrate is formed of a material suitable for three-dimensional (3D) printing.

9. The MRI system of claim 1 wherein the hemispherical spiral pattern includes a plurality of spiral turns around the contour of the portion of the subject to be imaged and wherein a distance between adjacent spiral turns of the at least one coil is uniform.

10. A transmit and receive coil system for performing a magnetic resonance imaging (MRI) process using an MRI system, the coil system comprising:
 a substrate configured to follow a contour of a portion of a subject to be imaged by the MRI system; and
 at least one transmit and receive coil coupled to the substrate and forming a three-dimensional spiral pattern extending over the substrate; wherein the three-dimensional spiral pattern includes a distance between adjacent portions of the at least one coil that is uniform,
  wherein the at least one transmit and receive coil is configured to originate and spiral out from a center point configured to be aligned on an apex of a crown of a head of the subject,
  wherein the at least one transmit and receive coil is further configured by spiraling out to extend to encircle a perimeter of the head of the subject.

11. The transmit and receive coil system of claim 10 wherein the at least one coil is sized to image a periphery of the subject.

12. The transmit and receive coil system of claim 10 wherein the substrate forms a helmet and the portion of the subject is the head, such that the helmet is configured to contour the head of the subject.

13. The transmit and receive coil system of claim 10 wherein the substrate is formed of a material suitable for three-dimensional (3D) printing.

14. The transmit and receive coil system of claim 10 wherein the three-dimensional spiral pattern includes a plurality of spiral turns around the contour of the portion of the subject to be imaged and wherein a distance between adjacent spiral turns of the at least one coil is uniform.

15. A single channel radio-frequency coil configured for a portion of human anatomy, the single channel radio-frequency coil comprising:
 a conductor arranged in a three-dimensional geometry about a region of interest, wherein the three dimensional geometry includes a distance between adjacent portions of the conductor that is uniform, and wherein, when the single channel radio-frequency coil is operated as a transmit and receive coil in conjunction with performing magnetic resonance of the portion of the human anatomy of a subject, the conductor is configured to produce and detect magnetic fields substantially parallel to a longitudinal axis of the subject's body,
 wherein the conductor is configured to originate and spiral out from a center point configured to be aligned with an apex of a crown of a subject's head,
 wherein the conductor is further configured by spiraling out to extend to encircle a perimeter of the subject's head.

16. The single channel radio-frequency coil of claim 15, wherein the conductor is arranged in a substantially spiral geometry.

17. The single channel radio-frequency coil of claim 15 configured as a head coil comprising a substrate formed to accommodate the subject's head, wherein the conductor is arranged in the three-dimensional geometry over a surface of the substrate.

18. The single channel radio-frequency coil of claim 17, wherein the conductor is arranged over at least a hemisphere of the substrate.

19. The single channel radio-frequency coil of claim 15, wherein the conductor is formed by a wire arranged in the three-dimensional geometry.

20. The single channel radio-frequency coil of claim 19, wherein the wire is a single-strand wire.

21. The single channel radio-frequency coil of claim 19, wherein the wire is a Litz wire.

22. The single channel radio-frequency coil of claim 15, wherein the conductor has a length greater than a meter.

23. The single channel radio-frequency coil of claim 22, wherein the conductor has a length greater than 5 meters.

24. The single channel radio-frequency coil of claim 23, wherein the conductor has a length greater than 10 meters.

25. The single channel radio-frequency coil of claim 15, wherein the conductor is arranged in the three-dimensional geometry such that the conductor forms at least 10 turns.

26. The single channel radio-frequency coil of claim 15, wherein the conductor is arranged in the three-dimensional geometry such that the conductor forms at least 20 turns.

27. The single channel radio-frequency coil of claim 15, wherein the conductor is arranged in the three-dimensional geometry such that the conductor forms at least 30 turns.

28. The single channel radio-frequency coil of claim 15, wherein the radio-frequency coil is configured to transmit and receive at frequencies corresponding to a B0 field of less than 0.2 T.

29. The single channel radio-frequency coil of claim 15, wherein the conductor is arranged in the three-dimensional geometry such that the conductor forms a plurality of spiral turns around the region of interest and wherein a distance between adjacent spiral turns of the conductor is uniform.

* * * * *

UNITED STATES PATENT AND TRADEMARK OFFICE
CERTIFICATE OF CORRECTION

PATENT NO. : 10,527,689 B2
APPLICATION NO. : 15/125860
DATED : January 7, 2020
INVENTOR(S) : Matthew S. Rosen et al.

Page 1 of 1

It is certified that error appears in the above-identified patent and that said Letters Patent is hereby corrected as shown below:

In the Specification

Column 7, Line 64, "ND" should be --A/D--.

Signed and Sealed this
Twenty-fifth Day of February, 2020

Andrei Iancu
*Director of the United States Patent and Trademark Office*